United States Patent [19]
Peterson

[11] 3,986,401
[45] Oct. 19, 1976

[54] COMPOSITE SAMPLING METHOD AND SYSTEM

[75] Inventor: Edward John Peterson, Castanea, Pa.

[73] Assignee: The United States of America as represented by the Secretary of the Interior, Washington, D.C.

[22] Filed: Oct. 14, 1975

[21] Appl. No.: 622,344

[52] U.S. Cl. ............................................. 73/421 B
[51] Int. Cl.² ........................................ G01N 1/14
[58] Field of Search ......... 73/421 B, 421 R, 422 TC

[56] References Cited
UNITED STATES PATENTS

| | | | |
|---|---|---|---|
| 3,412,612 | 11/1968 | Carr .................................. | 73/421 B |
| 3,589,197 | 6/1971 | Brooks, Sr. ........................ | 73/421 B |
| 3,896,673 | 7/1975 | Audouze et al. .................. | 73/421 B |
| 3,901,084 | 8/1975 | Brailsford ......................... | 73/421 B |
| 3,924,471 | 12/1975 | Singer .............................. | 73/421 B |

Primary Examiner—Richard C. Queisser
Assistant Examiner—Joseph W. Roskos
Attorney, Agent, or Firm—Gersten Sadowsky; Donald R. Fraser

[57] ABSTRACT

A method and system for collecting fluid samples from a high velocity effluent comprises a pump which is periodically energized to draw the fluid through a sample chamber and into a collection container. The sample chamber comprises four valves which are operated automatically in response to negative hydraulic pressure generated by the pump, viz: an inlet valve for receiving fluid from the sampling point, a first outlet valve connected to the pump, a second outlet valve for draining the fluid samples to the collection container and an air release valve. During a sampling cycle, with the pump energized, fluid is drawn from the sampling point at a velocity greater than or equal to that of the effluent. The fluid is directed through the inlet and first outlet valves of the sample chamber and to a reservoir. At the end of the sampling cycle, with the pump de-energized, a fixed volume of the fluid remaining in the sample chamber is drained into the collection container through the second outlet valve. The pump is periodically energized by timer means so that fluid samples are collected throughout the day.

11 Claims, 3 Drawing Figures

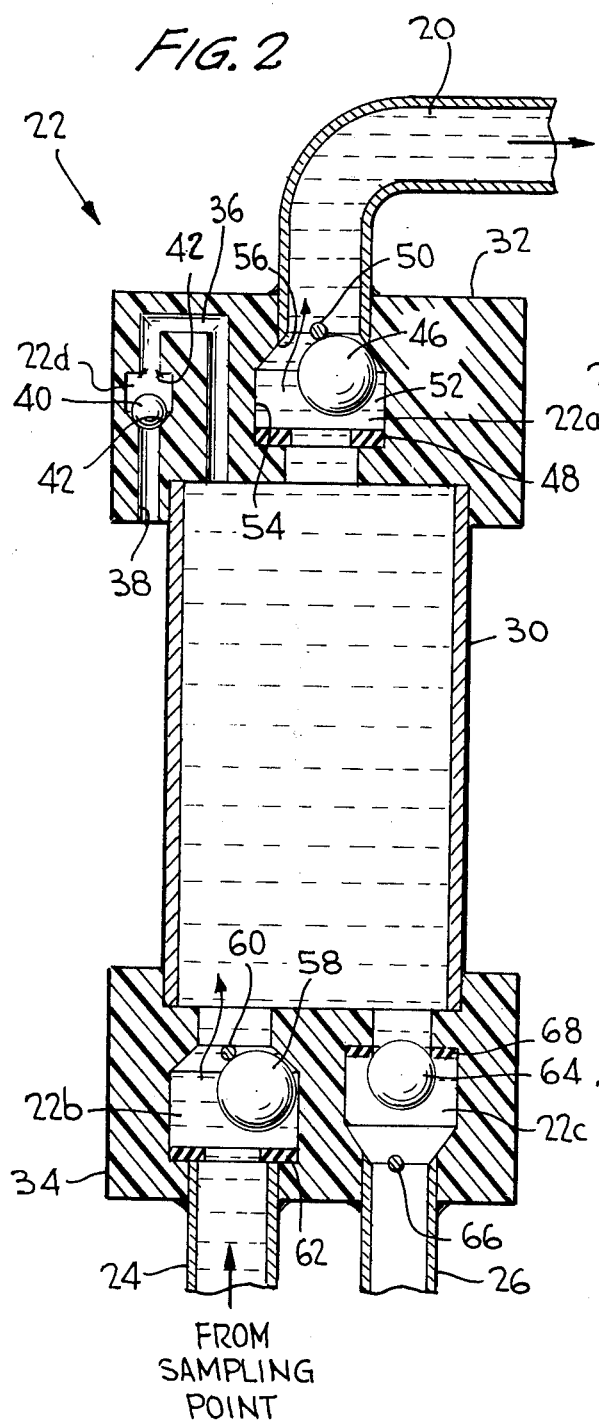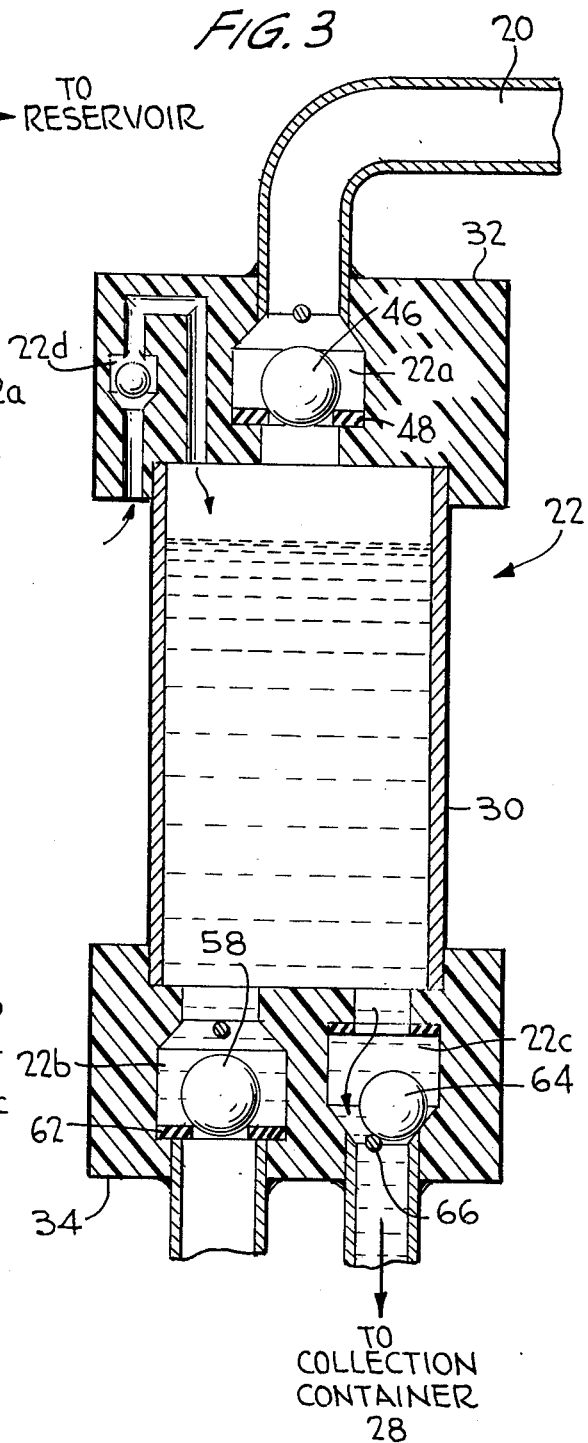

COMPOSITE SAMPLING METHOD AND SYSTEM

BACKGROUND OF THE INVENTION

The present invention relates generally to instruments for sampling fluids for analysis, and more particularly to a composite sampler which automatically collects fluid samples from high velocity sampling points without damaging particulate matter suspended therein or biasing the sample.

In the operation of a fish hatchery, it is often necessary to treat the hatchery water polluted by the build-up of waste matter of fish. Typically, grab samples are taken from hatchery water effluent every one-half hour around the clock in order to determine the amount of quality of solids present in the hatchery water. This procedure requires that a technician be on hand to perform the sampling.

In order to relieve the technician, automatic pump-driven composite samplers have been provided which periodically draw a sample of the hatchery water at a discharge tube into a collection container. The automatic composite samplers of the prior art, of which I am aware, have been somewhat unsatisfactory because the effluent at the discharge tube is actually drawn at low velocity through the pump on way to the sample chamber. The action of the pump destroys or alters the particulate matter. Also, the flow velocity of the water drawn with the sample chamber is less than that of the high velocity discharge, and a pressure head or "cone of rejection" is created at the chamber inlet tube. The effect of the pressure head is to bias the sample, i.e., draw a sample having less particulate matter than is representative of the discharge. Since proper analysis of the composite dictates that the suspended particulate matter be unadulterated and the samples be unbiased, the samples actually collected by prior art apparatus are inadequate.

Some prior art automatic composite samplers avoid damaging the suspended particulate matter in the sample by providing a sample chamber and locating the pump downstream of the chamber. The pump creates a negative pressure in the sample chamber, and draws the fluid up into the chamber for subsequent drainage into a collection container. The composite never reaches the pump so that the particulate matter is not altered or damaged. However, these systems are primarily adapted to be used in conjunction with static fluids. Accordingly, the velocity of fluids drawn by these apparatus is substantially lower than the velocity of effluent from a fish hatchery. The result is that the sample is biased.

Automatic composite samplers of which I am aware are disclosed in the U.S. Pat. Nos. to Carr 3,412,612 and Brooks, Sr. 3,589,197. While these systems function somewhat satisfactorily, each includes valves which must be operated by an external control means and is therefore relatively complex. For example, in Brooks, Sr., a flexible tube-type valve is controlled by an electrical solenoid which, along with the pump, is controlled by a timer. In Carr, a multi-valve sample chamber is controlled by a pair of electrical solenoids. The pair of solenoids is controlled by a timer; there is no pump and, in order to in-draw fluid, the sample chamber must be maintained beneath the surface of the fluid reservoir being sampled. The requirement of external control for the valves increases the cost and required maintenance of the samplers, and makes them unsuitable for low cost, high reliability applications. Neither Brooks, Sr. nor Carr discloses the use of a high velocity pump to eliminate biasing in the samples.

OBJECTS OF THE INVENTION

Accordingly, a primary object of the present invention is to provide a low cost, highly reliable, automatic, composite sampler.

Another object of the present invention is to provide a new and improved pump operated composite sampler which periodically collects composite samples without technician intervention.

Another object of the present invention is to provide a new and improved pump operated composite sampler, wherein particulate matter contained in the samples is not altered or biased.

Another object of the present invention is to provide a new and improved automatic composite sampler, wherein no external control means is required to operate the flow valves of a sample chamber.

Another object of the present invention is to provide a new and improved pump operated composite sampler, wherein flow valves are automatically controlled in response to pressure differentials generated by the pump.

SUMMARY OF THE INVENTION

In accordance with the present invention, a composite sampler comprises a high velocity electric pump for drawing fluid such as water from a high velocity hatchery discharge into a sample chamber having inlet and outlet valves controlled by a negative hydraulic pressure generated by the pump. During a sampling cycle, the negative hydraulic pressure in the sample chamber, generated by the pump, opens an inlet valve and a first outlet valve of the chamber to establish high velocity fluid flow from the sampling point at the discharge, through the sample chamber and pump, and back to a reservoir. The term "high velocity" connotes that the fluid is drawn into the sample chamber at a flow velocity equal to or greater than the flow velocity of the fish hatchery discharge to avoid biasing the samples. When the pump is de-energized at the end of the sampling cycle, the force of gravity and back pressure close the inlet and first outlet valves and open a second outlet valve and an air release valve in the sample chamber to drain the contents of the chamber to a collection container.

A timer controls a relay which periodically energizes the pump for a predetermined time duration so that over a long period of time, e.g., one day, a large number of periodically taken samples is deposited in the collection container. The samples drained into the collection container do not pass through the pump. Accordingly, there is no mastication of particulate matter in the samples.

Still other objects and advantages of the present invention will be readily apparent to those skilled in this art from the following detailed description, wherein I have shown and described only a preferred embodiment of the invention, simply by way of illustration of the best mode contemplated by me of carrying out my invention. As will be realized, the invention is capable of other and different embodiments, and its several details are capable of modification in various obvious respects, all without departing from the invention. Accordingly, the drawings and description are to be regarded as illustrative in nature, and not as restrictive.

BRIEF DESCRIPTION OF THE DRAWINGS

FIG. 2 illustrates a cross-sectional view of the sample chamber, shown in FIG. 1, with the ball-valves actuated by a negative pressure generated by the pump; and FIG. 3 illustrates a cross-sectional view of the sample chamber with the ball-valves deactuated.

BRIEF DESCRIPTION OF A PREFERRED EMBODIMENT

Figure 1:
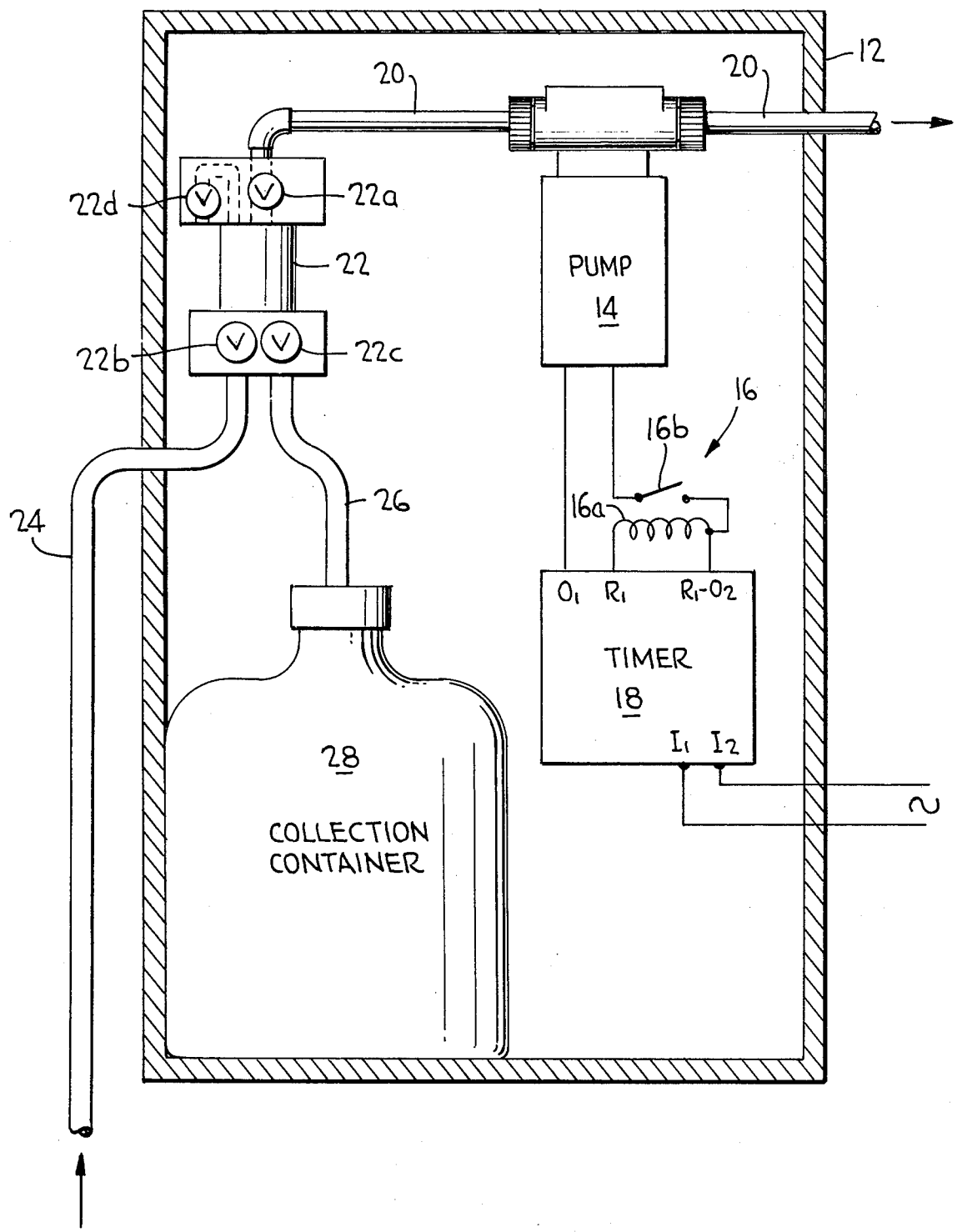
FIG. 1 illustrates a preferred embodiment of the invention.

Referring to FIG. 1, composite sampler 10, in accordance with the invention, includes a rectangular housing 12 containing a high velocity pump 14 secured to the wall of the housing. High velocity pump 14, which may be a "FLOWTEC" Model F-360 pump manufactured by Industrial Plastics, is energized by the AC power line through relay 16. The pump 14 creates negative pressure or suction sufficient to cause relatively high velocity fluid flow therethrough. The term "high velocity fluid flow" is used to connote fluid flow having velocity greater than or equal to the flow velocity of fish hatchery effluent or discharge, i.e., at least four feet per second. Obviously, however, the present invention can also be applied to the sampling of static fluids. A timer 18 is connected between relay 16 and the AC power line to periodically close the relay energizing pump 14.

Timer 18 is a conventional electrically operated timer, such as the Dayton Model 2-E-130 timer unit, having an internal set of cams to close an electrical circuit for a preselected duty cycle and a cycle duration. AC power is supplied at input terminals $I_1$ and $I_2$ of timer 18. One side of the power line is connected directly to pump 14 from timer output terminal $O_1$. The other power line to pump 14 is connected to output terminal $R_1$–$O_2$ of timer 18 through relay terminals 16b. Actuating coil 16a of relay 16 is connected between terminals $R_1$ and $R_1$–$O_2$ of timer 18. Whenever a switch (not shown) within timer 18 is closed, determined by the internal camming of the timer, relay coil 16a is energized by the AC power line and closes relay terminals 16b to supply full line voltage across pump 14. At the end of a sampling cycle, coil 16a is de-energized by timer 18, and in response thereto, relay terminals 16b open to de-energize pump 14.

Although timer 18 and pump 14 are shown as being power line operated, that is, designed to operate from a 120 volt 60 Hertz line, it is to be understood that pump 14 and timer 18 could be battery rather than line operated, if desired. Furthermore, pump 14 and timer 18 could, if desired, be operated by stepped-down, rectified line power with a battery (not shown) included as a stand-by source of power, in case of failure of the AC power line.

A tube 20 extends between pump 14 and a multi-wave sample chamber 22 at a first outlet valve 22a. In addition to first outlet valve 22'a, sample chamber 22 includes an inlet valve 22b, a second outlet valve 22c and an air release valve 22d. The operation of valves 22a–22b, forming an important aspect of the invention, is discussed in detail below.

A tube 24 is connected between a fluid sampling point in the hatchery effluent (not shown) and inlet valve 22b of sample chamber 22. The inlet end of tube 24 is directed upstream in the effluent. Another tube 26 is connected between second outlet valve 22c and collection container 28. Tubes 20, 24 and 26 are preferably formed of a flexible plastics material, such as polyethylene, but could be formed of a suitable material, such as copper.

Although the operation of composite sampler 10 and particularly sample chamber 22 will be described in detail below in conjunction with FIGS. 2 and 3, as an overview, pump 14 is periodically energized for a predetermined time interval controlled by timer 18. During a sampling cycle, with pump 14 energized, a negative hydraulic pressure is generated in sample chamber 22. The negative hydraulic pressure causes valves 22d and 22c to close, and valves 22b and 22a to open establishing a high velocity fluid flow path from the sampling point, through tube 24, sample chamber 22, tube 20, pump 14 and to a reservoir (not shown) through tube 20. Since valves 22a–d are controlled by the negative hydraulic pressure generated by pump 14, no external control means such as solenoids is needed. With pump 14 de-energized at the end of a sampling cycle, (under the control of timer 18) there is no negative hydraulic pressure in sample chamber 22, and the force of gravity and back pressure close valves 22a, 22b and opens 22d. Valve 22c, which is a normally open valve, drains the fluid remaining in sample chamber 22 to collection container 28.

The volume of sample chamber 22 (which depends upon the volume of cylinder 30) is a predetermined fixed volume, such as 100 milliliters, whereby at the end of each sampling cycle, collection container 28 retains 100 milliliter samples of fluid. The volume of collection container may be 10 liters, for example, and therefore capable of containing a composite sample comprising up to 100 individual samples of the hatchery water. As described below, cylinder 30 is interchangeable and may be replaced by a cylinder having a volume larger or smaller than 100 milliliters.

Referring to FIGS. 2 and 3, the operation of sample chamber 22 is described in more detail. Sample chamber 22 comprises a rigid cylinder 30 containing a predetermined volume (100 milliliters) for collecting a corresponding volume of fluid for transfer to collection container 28. Attached to opposite ends of cylinder 30 are end blocks 32 and 34 formed of an acrylic plastic, or of a light weight metal such as aluminum. Block 32 and 34 may be of one-piece construction, as shown, or may be laminated, with the laminations being bonded or bolted together. Also, blocks 32 and 34 as well as the ends of cylinder 30 may be threaded such that the blocks and cylinder are removably secured together. This permits cylinders of different volumes to be selectively attached to blocks 32 and 34 depending on the desired sample volume.

Upper block 32 contains air relief valve 22d and outlet valve 22a. Air relief valve 22d is located in a U-shaped air passageway 36 extending between cylinder 30 and an egress 38 formed in one face of block 32. Valve 22d is preferably a conventional, normally open ball valve assembly comprising steel ball 40, valve seal 42. Steel ball 40 is normally seated against frusto-conical face by the force of gravity, allowing air flow, but is drawn up against seal 42 when a negative hydraulic pressure is created within sample chamber 22 during operation of pump 14 (FIG. 1).

Similarly, outlet valve 22a is normally closed with steel ball 46 seated against ring seal 48 blocking fluid flow but the valve is opened with the ball drawn up against pin 50 during operation of pump 14. The upper side wall 56 of valve 22a, is frusto-conical, while the lower side wall 54 containing seal 48 is cylindrical.

Tube 20 engages the upper distal portion of valve side wall 56. In the open position, ball 46 is maintained between frusto-conical wall 56 and pin 50 adjacent tube 20 permitting fluid flow through valve 22a as shown by the arrow.

Lower block member 34 has formed therein inlet valve 22b and second output valve 22c. Valves 22b and 22c are identical in configuration to each other and to valve 22a, but are inverted relative to each other with valve 22b being normally closed and valve 22c being normally open. Valve 22b contains steel ball 58 which abuts either pin 60 or seal 62, depending upon whether there is a negative hydraulic pressure in sample chamber 22. Similarly, valve 22c contains nylon ball 64 which is seated against either pin 66 or seal 68.

Tubes 20, 24 and 26 are sealed to blocks 32 and 34 respectively at valves 22a, 22b and 22c, by threading, friction fitting or crimping if the tubes are formed of copper, or by bonding if the tubes are formed of flexible polyethylene. If necessary, a suitable sealing compound, such as RTV, may be added, as shown in FIGS. 2 and 3, at the tube-block interfaces to prevent fluid leakage.

Referring again to FIG. 1, periodically (e.g. every one-half hour), pump 14 is energized for a predetermined time duration (e.g., 15 seconds) under control of timer 18. At the start of a sampling cycle, operation of pump 14 creates a negative hydraulic pressure in tube 20 relative at atmospheric pressure, resulting in suction adequate to bring steel balls 46, 58 and 40 and nylon ball 64 to their upper positions respectively in valves 22a, 22b 22d and 22c (see FIG. 2). A high velocity fluid flow path is established respectively from the effluent sampling point (not shown), through tube 24, valves 22b and 22a, tube 20, pump 14 and to a reservoir. Since air passageway 36 is blocked by steel ball 40 contained in air relief valve 22d when in its closed position it prevents loss of prime through the air relief valve. It should be noted that during flow of the fluid through sampler 22, chamber 30 is at all time completely filled wiith fluid.

Of particular importance, with pump 14 energized, fluid is drawn into tube 24 at a flow velocity that is greater than or equal to the flow velocity of the effluent. The effect is to eliminate any "depletion cone" from arising at the inlet of tube 24, and thus avoid biasing of the sample.

However, referring now to FIG. 3, when pump 14 is de-energized at the end of a sampling cycle under control of timer 18, there is no negative hydraulic pressure created in tube 20 and sample chamber 22, and steel balls 46, 58, 40 and nylon ball 64 drop, under the force of gravity and back pressure, to their lower positions respectively in valves 22a, 22b 22d and 22c. More specifically, steel ball 46 seats against seal 48 in valve 22a, steel ball 58 seats against seal 62 in valve 22b and nylon ball 64 abuts pin 66 in valve 22c. In this condition, there is a flow path extending only through valve 22c, i.e., from cylinder 30 to collection container 28 (see arrow). Thus, the fluid sample retained in chamber 30 at the instant that pump 14 is de-energized drains into collection container 28 through valve 22c and tube 26. Gravity on steel ball 40 opens air relief valve 22d to permit air to enter cylinder 30 as the fluid drains.

Since valve 22b is sealed by ball 58, no fluid returns to the reservoir through tube 24. Cylinder 30 of sample chamber 22 empties its fluid contents completely into collection container 28; there is no additional fluid flow through inlet valve 22b until the start of another sampling cycle. At that time, a fluid flow path is once again established from the sample point, through sampler 22, pump 14 and to the reservoir, as shown in FIG. 2. In practice, I sustain fluid flow through cylinder 30 for at least 15 seconds to purge the system until another sample is drained into collection container 28.

In this disclosure, there is shown and described only the preferred embodiment of the invention, but, as aforementioned, it is understood that the invention is capable of use in various other combinations and environments, and is capable of changes or modifications within the scope of the inventive concept as expressed herein. For example, although valves 22a-d have been illustrated as ball valves, they could be any other suitable valve, such as conventional flapper valves. Also, although the invention has been illustrated with respect to sampling hydraulic fluids it is to be understood that the invention can be applied to the sampling of gases without altering particulate matter suspended therein.

What is claimed is:

1. Apparatus for automatically collecting fluid samples from an effluent comprising a pump, timer means for periodically operating said pump for a predetermined time duration, a collection container for storing said fluid samples, and valve means disposed between said pump and a sampling point, said valve means including a plurality of valves and a sample chamber wherein fluid flow with respect thereto is controlled by said valves the actuation of which is occasioned by fluid pressure generated by said pump, said valve means establishing a first fluid flow path including said sampling point, said valve means and said pump in response to the presence of said fluid pressure, and a second fluid flow path including said valve means and said collection container in the absence of said fluid pressure.

2. The apparatus of claim 1 wherein said sample chamber has a volume equal to a predetermined fixed volume of each of said fluid samples.

3. The apparatus of claim 1, wherein said plurality of valves includes an inlet valve, first and second outlet valves and an air relief valve, said first flow path comprising said inlet valve along with said first outlet valve, and said second flow path comprising only said second outlet valve.

4. The apparatus of claim 1, wherein each of said valves comprises a ball valve.

5. The apparatus of claim 1, wherein said pump is a high velocity pump, the velocity of fluid in said first fluid flow path being greater than or equal to a flow velocity of said effluent.

6. The apparatus of claim 1, wherein said sample chamber further includes a cylinder, opposite ends of said cylinder being enclosed by block members containing said plurality of valves.

7. The apparatus of claim 6, wherein one of said block members contains said air relief and first outlet valves, and the other member contains said inlet and second outlet valves.

8. The apparatus of claim 7, wherein said sample chamber has a volume that is equal to a preselected volume of each of said fluid samples.

9. In an apparatus for automatically collecting fluid samples from an effluent, said apparatus being of the type comprising a pump for drawing said samples from a collecting point in said effluent for deposit into a collection container, and timer means for periodically energizing said pump for predetermined time durations, the improvement comprising a fluid flow control means having a sample chamber disposed between said sampling point and said pump and said sampling point and said collection container, and valve means whereof normally conditioned valves are actuated by hydraulic pressure generated in said pump through said fluid, said valve means establishing a first fluid flow path including said sampling point, said sample chamber and said pump when actuated in response to a presence of said generated hydraulic pressure, and a second fluid flow path including said sample chamber and said collection container when normally conditioned in an absence of said generated hydraulic pressure.

10. The apparatus of claim 9, wherein said valve means includes an inlet valve receiving fluid from said sampling point; a first outlet valve for directing fluid to said pump; a second outlet valve for directing fluid to said collection container and an air relief valve.

11. The apparatus of claim 10, wherein said valves are ball valves.

* * * * *